(12) United States Patent
Pomfrett (10) Patent No.: US 6,217,521 B1
(45) Date of Patent: Apr. 17, 2001

(54) ANALYSIS FOR THE PRESENCE OF DEGENERATIVE BRAIN DISEASE

(75) Inventor: Christopher Pomfrett, Sandbach (GB)

(73) Assignee: The Victoria University of Manchester, Manchester (GB)

(*) Notice: Subject to any disclaimer, the term of this patent is extended or adjusted under 35 U.S.C. 154(b) by 0 days.

(21) Appl. No.: 09/173,736

(22) Filed: Oct. 16, 1998

Related U.S. Application Data (63) Continuation of application No. PCT/GB97/01043, filed on Apr. 15, 1997.

(30) Foreign Application Priority Data

| | | |
|---|---|---|
| Apr. 17, 1996 | (GB) | 9607970 |
| Nov. 15, 1996 | (GB) | 9623759 |
| Mar. 1, 1997 | (GB) | 9704300 |
| Apr. 15, 1997 | (WO) | PCT/GB97/01043 |

(51) Int. Cl.[7] .............. A61B 5/0402; A22B 3/00
(52) U.S. Cl. .............. 600/484; 600/513; 452/52
(58) Field of Search .............. 452/52; 600/483, 600/484, 481, 513, 521

(56) References Cited

U.S. PATENT DOCUMENTS

| | | | | |
|---|---|---|---|---|
| 4,510,944 | * | 4/1985 | Porges | 600/500 |
| 5,372,140 | * | 12/1994 | Pomfrett | 600/513 |
| 5,807,687 | * | 9/1998 | Jackman et al. | 435/7.1 |

* cited by examiner

Primary Examiner—Kennedy Schaetzle
(74) Attorney, Agent, or Firm—Nixon & Vanderhye (57) ABSTRACT

A method for detecting for the presence of a degenerative brain disease such as BSE or CJD. A measurement is made of the respiratory sinus arrhythmia of any mammal which is suspected of suffering from the degenerative brain disease. It is assumed that the mammal is suffering from such a disease if the measured RSA is outside a predetermined reference range. The reference range may be determined from data which forms the basis for the calculation of the RSA range by applying a suitable test for randomness.

6 Claims, 7 Drawing Sheets

Summary Data
(Innoculated = Injected with BSE agent but not exhibiting clinical signs)

| Sample | SD | Mean R-R | Filtered FFT Area | Filtered FFT Peak |
|---|---|---|---|---|
| 9: BSE Sick | 7.5 | 588.5 | 0.00000007955 | 0.0000003 |
| 8: Innoculated | 18.04 | 634.2 | 0.00000164888 | 0.0000296 |
| 5: Innoculated | 48.1 | 599.4 | 0.00000207863 | 0.0000682 |
| 3: Innoculated | 36.7 | 585.9 | 0.00000401380 | 0.0000644 |
| 10: No BSE | 41.03 | 717 | 0.00000512334 | 0.0000018 |
| 7: Innoculated | 54.8 | 775.3 | 0.00000564718 | 0.0002206 |
| 2: No BSE | 50.2 | 837.1 | 0.00000671718 | 0.0001632 |
| 4: Innoculated | 39.9 | 619.9 | 0.00001527400 | 0.0004497 |
| 1: BSE Intermediate | 37.8 | 675.4 | 0.00001753720 | 0.0004821 |
| 6: BSE Terminal | 132.1 | 948.5 | 0.00003781990 | 0.0012770 |

ANALYSIS FOR THE PRESENCE OF DEGENERATIVE BRAIN DISEASE

This is a continuation of PCT application No. PCT/GB97/01043, filed Apr. 15, 1997.

BACKGROUND OF THE INVENTION

The present invention relates to analysis for the presence of degenerative brain disease.

Increasing public and scientific concern has been expressed about the possibility of bovine spongiform encephalopathy (hereinafter BSE) being transmitted to the human population as a result of consumption of products derived from infected cattle. It has been postulated that British cattle have become infected with BSE as the result of eating feed including products derived from sheep that have been infected with scrapie. It has also been postulated that BSE has developed as the result of the nervous systems of cattle being damaged by pesticides. Regardless of the origins of the disease, it has been suggested that cattle suffering from BSE should be slaughtered and their carcasses should not be introduced into the human food chain.

Given that BSE takes typically five or more years to become manifest as the result of the behaviour of an infected animal, and that there has heretofore been no accepted method of assessing the probability of whether or not a particular cow is suffering from BSE other than examining the brain of the slaughtered animal, it has been suggested that the only safe approach to adopt which will in addition calm public fears about the safety of eating beef products is widespread slaughter. It is almost inevitable that such a policy will result in the slaughter of many thousands of cattle which are not infected with BSE.

It is known that information regarding the status of the central nervous system of mammals can be derived from the quantification of heart rate variability. For example, the paper "Respiratory sinus arrhythmia during recovery from isoflurane-nitrous oxide anaesthesia" by Donchin, Feld, and Porges, Anesth Analg 1985; 64:811–15 states that respiratory sinus arrhythmia (hereafter RSA) may provide a physiological index of the level of anaesthesia. That same paper refers to work dating back to as early as 1935 which indicated that RSA disappeared during the induction of ether anaesthesia.

It is also known that RSA is suppressed in diabetics. Details of a method for measuring RSA to enable the identification of diabetics which method relies upon the application of circular statistics to data derived from patients is given in the paper "RR-variation: the autonomic test of choice in diabetes", by Genovely and Pfeifer, Diabetes/Metabolism Reviews, volume 4, No. 3, 255–271(1988), John Wiley & Sons Inc.

Published International Patent Application No. WO92/06632 describes a method of monitoring the depth of anaesthesia by deriving a measurement of RSA from an analysis of the position of R-waves relative to the respiratory cycle and comparing the measured RSA with a reference value obtained from the analysed series of R-waves. This method provides a reliable indication of the depth of anaesthesia which is of use to an anaesthetist as the measure of the depth of anaesthesia can be obtained sufficiently quickly for that measurement to be used in the control of the administration of anaesthetics.

It is apparent from the above documents and references cited in those documents that RSA variation provides an indication of the state of the cardiovascular autonomic nervous system function and that the measurement of RSA may be of value in assessing depth of anaesthesia and in the identification of diabetics.

A review of recent publication has been conducted in an attempt to understand the structural changes which occur in the brains of mammals infected with BSE and similar spongiform degenerative brains diseases such as Creutzfeldt-Jakob disease (CJD). The results are summarised below.

A paper by M. Jeffery and W. G. Halliday entitled "Numbers of neurons in vacuolated and non-vacuolated neuroanatomical nuclei in bovine spongiform encephalopathy—affected brains", Journal of Comparative Pathology 110(3):287–293 reports studies of the brains of seven cows affected by BSE. These studies revealed that in infected animals there was an inconsistent degree of neuronal perikaryonal vacuolation in the dorsal vagal nucleus.

The abstract of a paper by A. Yagishita entitled "Computered tomography of Creutzfeldt-Jakob disease", in the Journal Rinsho Hoshasen, 34(11)P1317–25, 1989, noted marked atrophy of the cortex, brainstem and cerebellum.

A paper by G. A. H. Wells and J. W. Wilesmith entitled "The neuropathology and epidemiology of the bovine spongiform encephalopathy", Brain Pathology, 5(1):91–103, 1995 refers to the histopathological diagnosis of BSE, validated on a section of the medulla, and to neuronal loss in BSE which may make an important contribution to functional deficits.

RSA is a measure of the activity in the reflex loop defined between the lungs, brain and heart. The lungs feed data to the medulla of the brain stem which produces outputs transmitted via the vagal nerve to the heart to control heart rate. This reflex control loop is disrupted in diabetics as a result of damage to the vagal nerve and is disrupted by the administration of anaesthetic as a result of depression of brain stem activity. The present invention is based on a realisation that BSE and similar degenerative brain diseases are likely to disrupt the operation of the lungs/brain/heart reflex control loop and, given that RSA is an indicator of disruption to that control loop, it can also be used as an indicator of BSE.

SUMMARY OF THE INVENTION

It is an object of the present invention to make use of an assessment of RSA in mammals to assist in the management of animal herds subject to degenerative brain diseases such as BSE.

According to the present invention, there is provided a method for estimating the probability that a mammal is suffering from a degenerative brain disease, wherein a measurement is made of the respiratory sinus arrhythmia of the mammal, and it is assumed that the mammal is suffering from a degenerative brain disease if the measured RSA is abnormal.

The invention also provides a method for selecting mammalian animals carcasses for introduction into the human food chain, wherein before slaughter the respiratory sinus arrhythmia of the animals to be slaughtered is measured, and only those carcasses from animals for which the associated RSA measurement is normal are selected.

The invention also provides a method for selecting mammalian animals for slaughter, wherein the respiratory sinus arrhythmia of the animals is assessed, and animals with an abnormal RSA are slaughtered.

The invention also provides a degenerative brain disease monitoring apparatus, comprising means for measuring the respiratory sinus arrhythmia of a mammal, and means for producing an output indicating that the mammal is suffering from a degenerative brain disease if the measured RSA is abnormal.

The invention also provides an animal carcass selection apparatus, comprising means for monitoring the respiratory sinus arrhythmia of animals prior to slaughter, and means for generating an output representing whether or not individual animals have normal RSA, the output being used to enable the selection of carcasses of only those animals for which the output indicates normal RSA.

The invention also provides a selection apparatus for selecting animals for slaughter, comprising means for monitoring respiratory sinus arrhythmia of the animals, and means for producing an output indicating which animals have an abnormal measured RSA to enable the slaughter of such animals.

It is believed that BSE and similar degenerative brain diseases generally characterised as being spongiform in nature result in lesions in the brain well before brain disfunction resulting from the progression of such lesions becomes apparent. Accordingly, although an assessment of the RSA of for example a cow cannot provide more than a rough guide as to whether or not that animal has BSE, it can be assumed that an animal with a normal RSA level is not suffering from the disease. Accordingly the invention provides an economically viable method of assessing animals such as cattle for degenerative brain diseases without it being necessary to slaughter the animal for the assessment to be made.

Various techniques are known for measuring RSA, for example those described in the patent specification and papers referred to above. The content of those documents is introduced herein by reference. For example, the paper by Genovely and Pfeifer referred to above sets out various analysis methods including the "mean circular resultant" method which relies upon the degree of clustering of R-waves relative to the respiratory cycle. This is a suitable method to be used in measuring RSA in methods in accordance with the present invention.

RSA may be measured in for example a cow by fitting an ECG monitor and a breathing monitor to the animal. Useful data representing the position in time of R-waves relative to the breathing cycle can be derived in minutes. That data can then be presented to a computer for rapid analysis to derive a measure of RSA, and that measure can be compared with a reference value or range to determine whether or not the animal should be treated as being BSE free. Thus the present invention can be applied in a cost-effective manner.

RSA may also be measured in other ways, for example by fitting only an ECG monitor to the animal, and analysing the spectral components of an ECG tachygram derived from the monitor, i.e. the beat to beat variations in heart rate. RSA appears as a high frequency peak coincident with the respiratory frequency.

It should also be noted that RSA disruption may be indicated by either an abnormally high or abnormally low level of RSA. For example, brain lesions could cut the respiratory input to the nucleus tractus solitarius (NTS), effectively eliminating RSA, or could cut the link between the NTS and the dorsal motor nucleus (DMNX), resulting in an abnormal amplification of RSA.

BRIEF DESCRIPTION OF THE DRAWINGS

An embodiment of the present invention will now be described, by way of example, with reference to the accompanying drawings, in which.

DETAIL DESCRIPTION OF PREFERRED EMBODIMENTS

Figure 1:
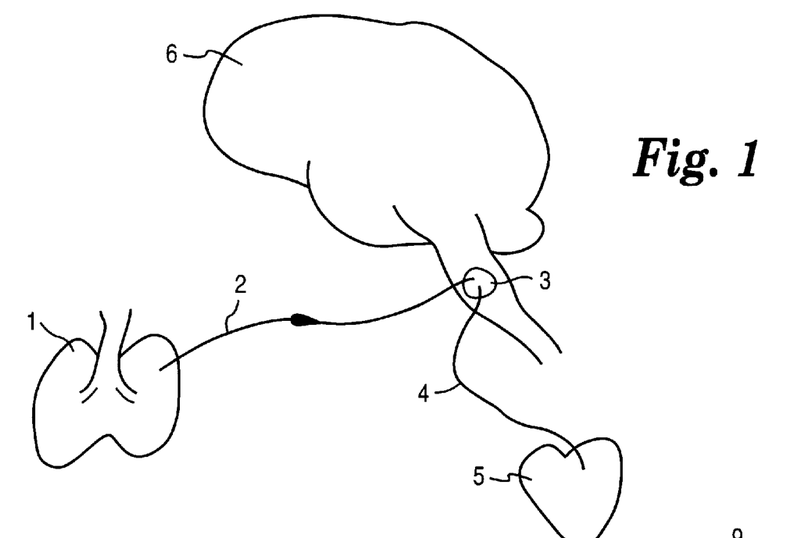
FIG. 1 is a schematic representation of the lungs/brain/heart control loop.
Figure 2:
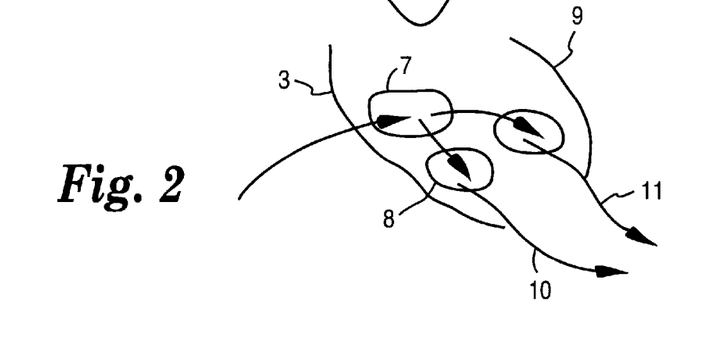
FIG. 2 is an illustration in greater detail of part of FIG. 1.

Referring to FIGS. 1 and 2, the lungs 1 expand and contract as a result of normal respiration. Stretch receptors in the wall of the lungs generate signals which are transmitted over nerves represented by line 2 to the brain stem or medulla 3. Signals from the medulla are transmitted on nerves represented by the line 4 to the heart 5. Damage to the medulla will also of course disrupt the transmission of signals from the cerebral cortex 6 but damage to the cerebral cortex will not directly affect the lungs/brain/heart control loop.

The medulla 3 incorporates the nucleus tractus solitarius (NTS), the nucleus ambiguus (NA) and the dorsal motor nucleus (DMNX). Signals from the lungs are delivered to the NTS which in turn supplies signals to the NA 8 and the DMNX 9. The NA and DMNX send separate signals on nerves represented by lines 10 and 11 to the heart.

It is believed that BSE and CJD and similar degenerative brain diseases reduce the numbers of neurons in the NTS, NA and DMNX nuclei. Any reduction in the numbers of neurons in these nuclei will inevitably suppress or otherwise disrupt the operation of the lungs/brain/heart control loop. RSA is an accurate representation of the stability of that control loop.

The present invention may be implemented using equipment identical to that described in the above mentioned International patent application which was originally intended for use in the monitoring of the depth of anaesthesia. Further information can be gained from that application, but in brief R-waves are detected, the position of those R-waves relative to the respiratory cycle is determined, and the degree of clustering of those R-waves relative to the respiratory cycles is assessed. The assessment of the degree of clustering is then compared with a reference value which represents the level of significance of the data, the level of significance being a function of the volume of data relied upon to produce the estimate of the degree of clustering.

Figure 3:
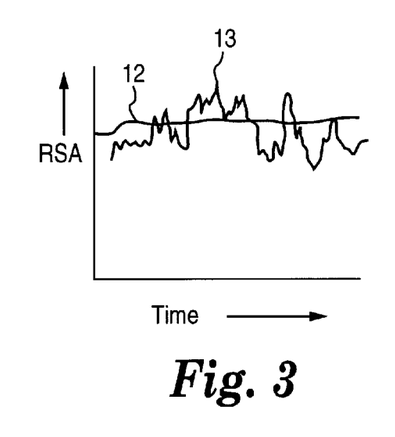
FIG. 3 is a representation of data obtained from a normal mammal.

FIG. 3 represents outputs which can be expected from a healthy mammal. The regular line 12 represents the reference level. The irregular line 13 represents the measured RSA. It will be noted that the two signals are of the same order of magnitude and that the signal 13 is sometimes greater than and sometime less than the reference level 12.

Figure 4:
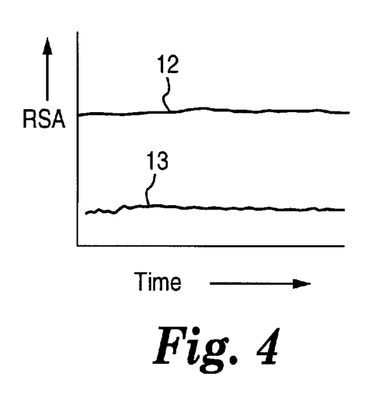
FIG. 4 is a representation of data to be expected from a mammal the condition of which is such that the lungs/brain/heart control loop has been severely disrupted so as to suppress RSA.

FIG. 4 represents outputs which can be expected from a mammal in which the lung/brain/heart control loop has been disrupted for example as a result of diabetes, anaesthesia or the formation of lesions in the brain stem. It will be noted that the line 12 remains much as it would be in a healthy subject. This indicates that good quality data is being assessed. In contrast, the line 13 indicates a greatly suppressed RSA level which is substantially constant over time. The two cases illustrated in FIGS. 3 and 4 are clearly distinguishable.

If a herd of cows is to be selectively killed to remove those cows which it is believed may be suffering from BSE, the individual cows could be assessed to produce plots corresponding to those illustrated in FIGS. 3 and 4. A cow showing results similar to those of FIG. 3 could be readily deemed uninfected with BSE whereas a cow showing results as shown in FIG. 4 might be suffering from BSE and therefore a decision might be taken to kill that cow and to prevent its carcass entering the food chain.

The representation data shown in FIGS. 3 and 4 could be produced in accordance with the method as described in the abovementioned International patent application, that is by analysing the degree of clustering of a series of R-waves relative to the respiratory cycles in which they occur, applying a test for randomness to the analysed series of R-waves to derive a reference value representing a predetermined significance level for clustering of the R-waves relative to the respiratory cycles, and comparing the reference value to the measurement value to derive a measure of the degree to which the lung/brain/heart control loop has been disrupted. An animal disposal procedure could be based on the assumption that if disruption has occurred it will be assumed that this results from the progress of a degenerative brain disease, and hence that animal will be destroyed and its carcass not admitted into the food chain.

A pilot study has been conducted to test the feasibility of making routine recordings of heart rate variability (HRV) in cows to assess RSA and thereby assess the probability of a particular cow having BSE.

A sample of ten cows was examined, the cows in the sample being selected from three groups, that is normal, inoculated with BSE but not exhibiting clinical signs, and animals exhibiting clinical signs of BSE. Each cow was positioned in a crush to facilitate handling. Standard electrocardiogram (ECG) electrodes were affixed to each of the cows in turn. The resultant ECG outputs were amplified using a standard amplifier and digitised using a standard laboratory interface. Three hundred seconds of ECG data was collected from each cow.

No respiratory signal was recorded with the ECG, so the level of RSA was derived by performing power spectral analysis on the ECG R—R wave interval, in order to estimate the amount of power within the respiratory frequency domain. Peak power and total power was derived for the frequency band 0.05 to 0.4 Hz. This deliberately wide band ensured that respiratory effects on HRV would be included in the analysis, at whatever frequency the cow was breathing. Standard software was used to analyse the resultant data.

Figure 5:
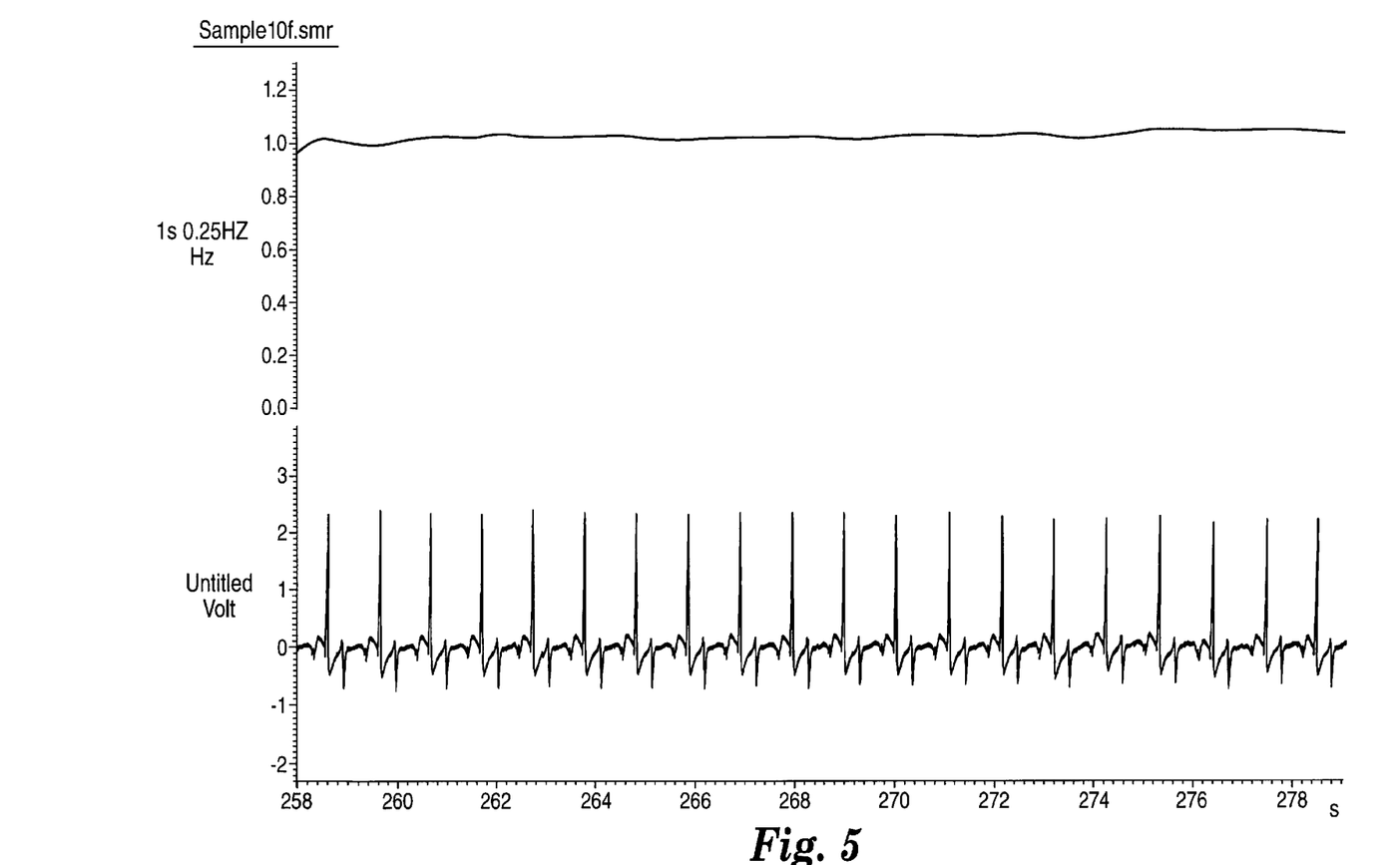
FIGS. 5 and 6 represent data obtained from a cow not infected with BSE.
Figure 6:
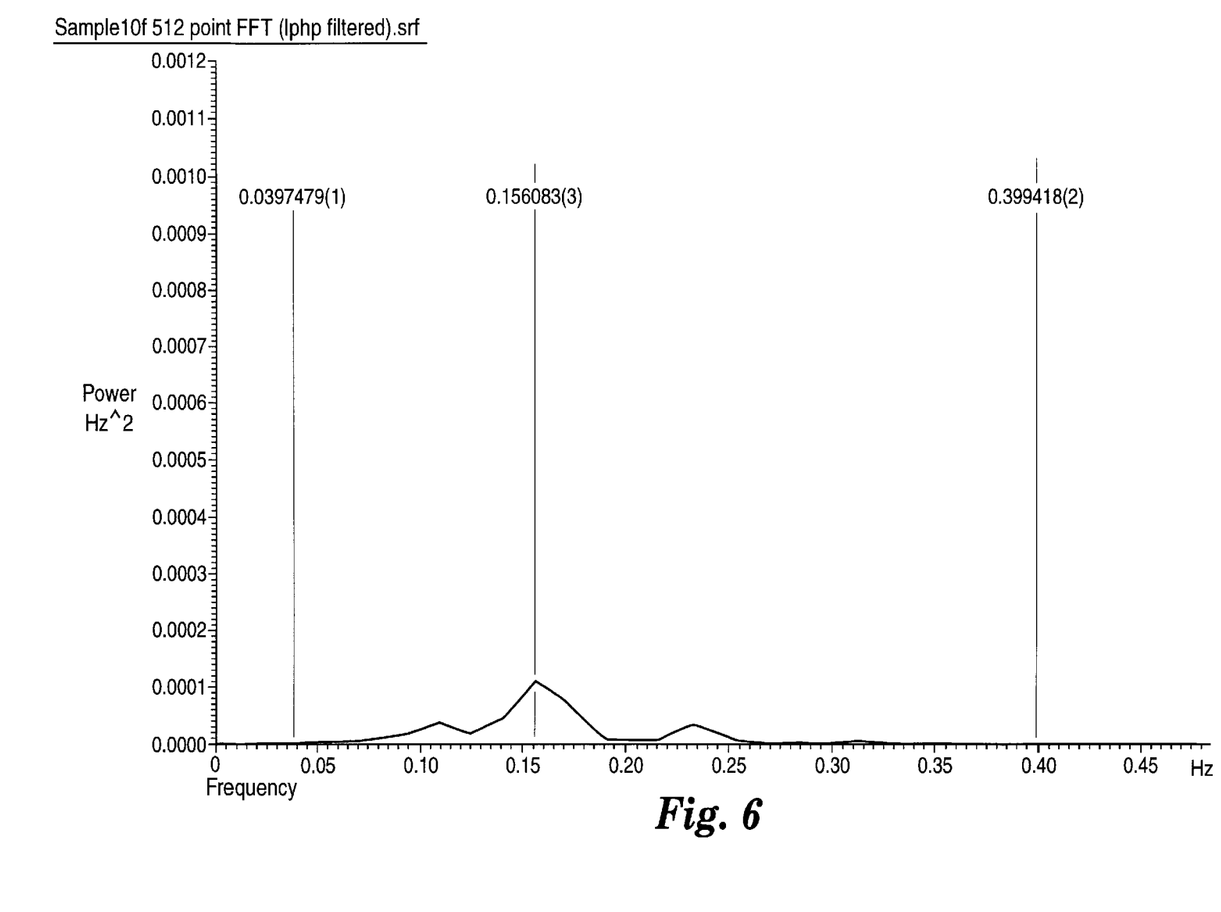
Figure 7:
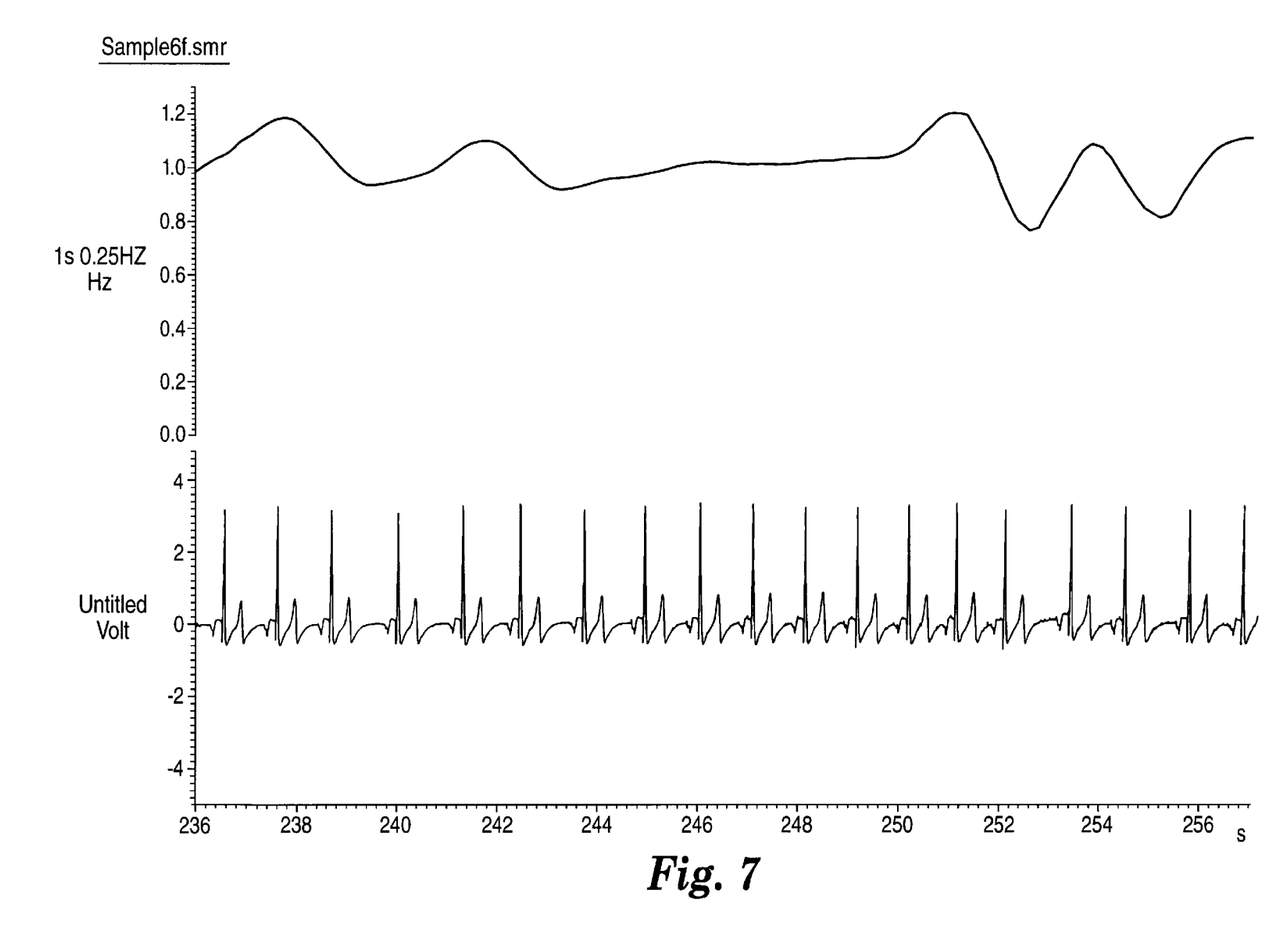
FIGS. 7 and 8 represent data obtained from a cow exhibiting visible symptoms of BSE.
Figure 8:
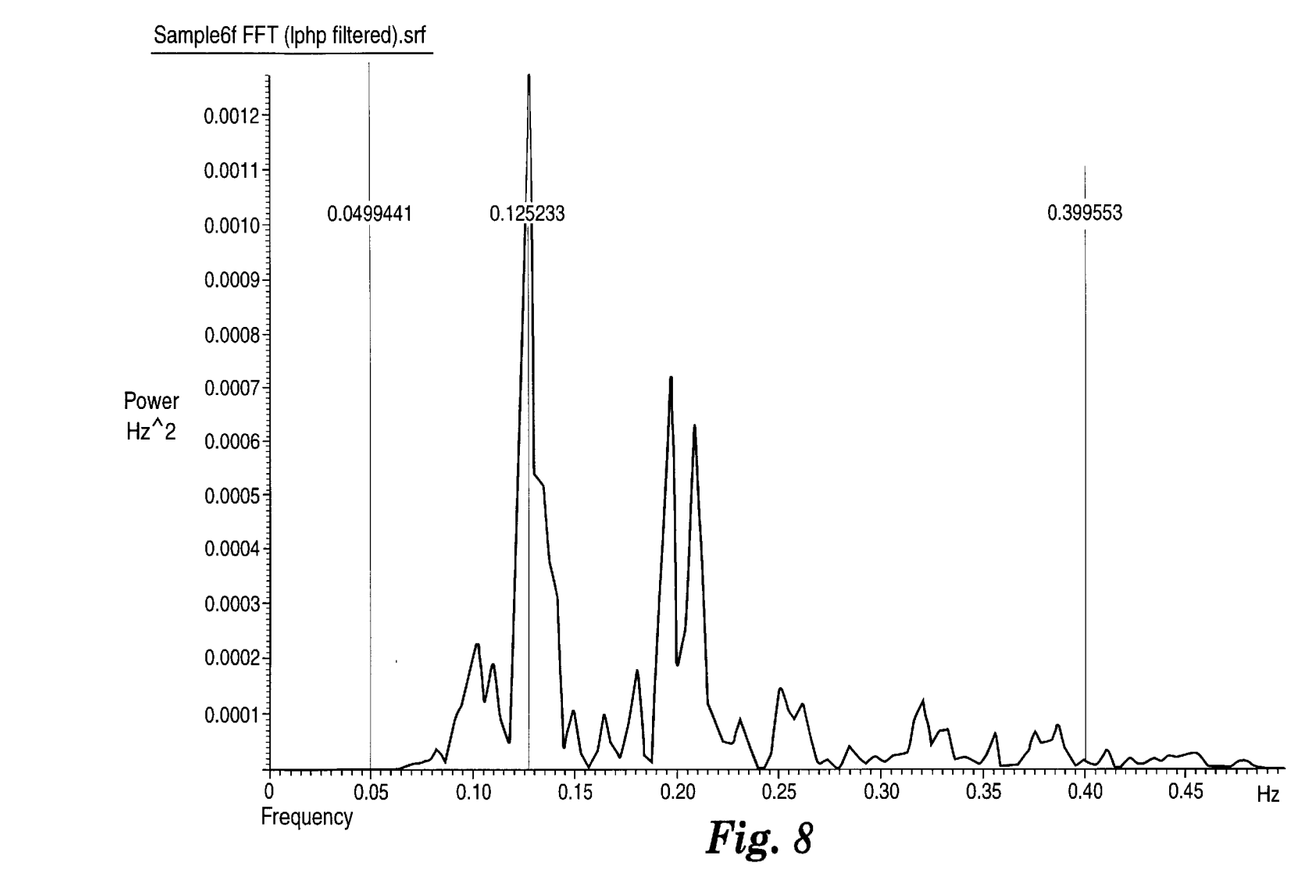

The data represented in FIGS. 5 and 6 was obtained from a cow not suffering from BSE. The data shown in FIG. 5 is in the form of the raw high resolution ECG output, and a tachygram showing the level of HRV (degree of variation in the upper line from the horizontal, more HRV being represented as more deviation in the line). FIG. 6 shows the 512 point FFT (low pass and high pass filtered) for the same data as represented by FIG. 5. FIGS. 7 and 8 present equivalent data derived from a cow exhibiting visible symptoms of BSE. The BSE infected cow clearly shows an abnormal level of HRV (and therefore RSA) in comparison with the normal cow.

Figure 9:
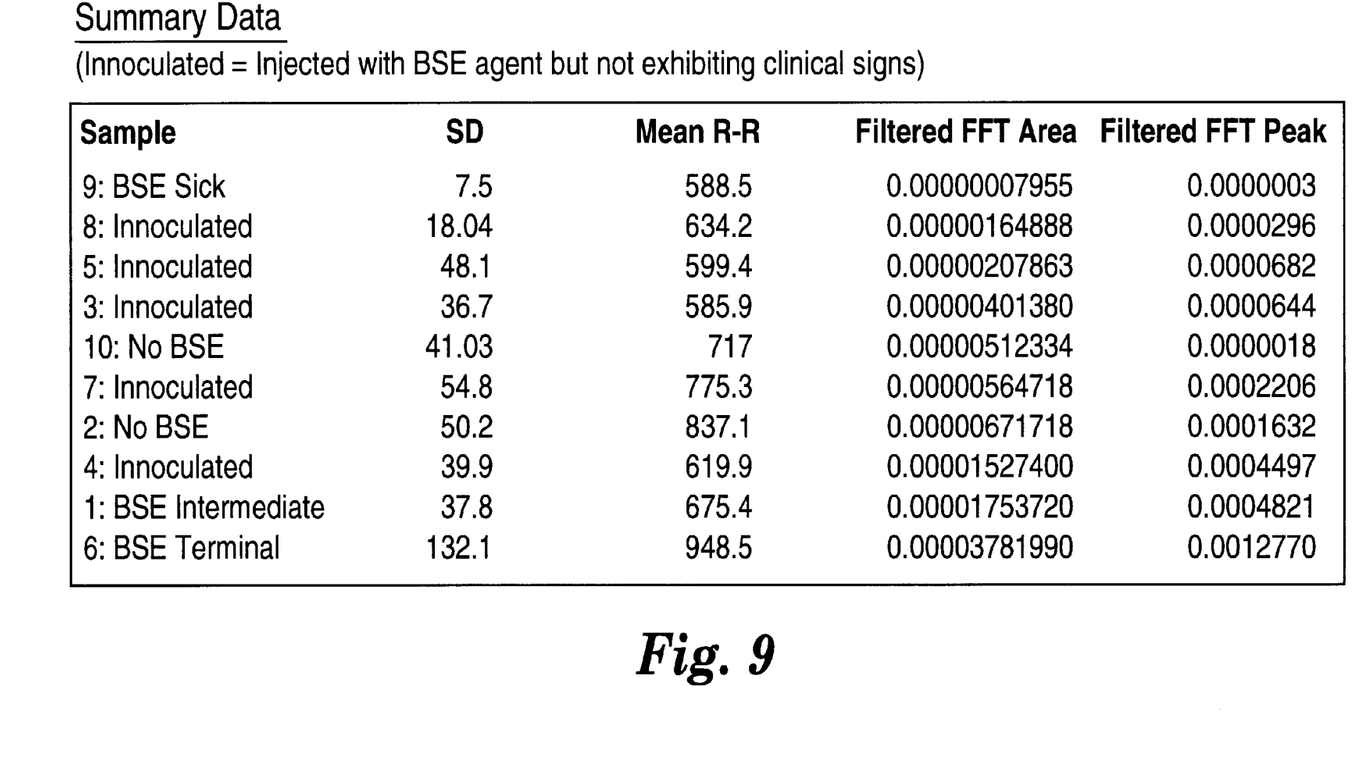
FIG. 9 is a table summarising data obtained from a sample of ten cows.
Figure 10:
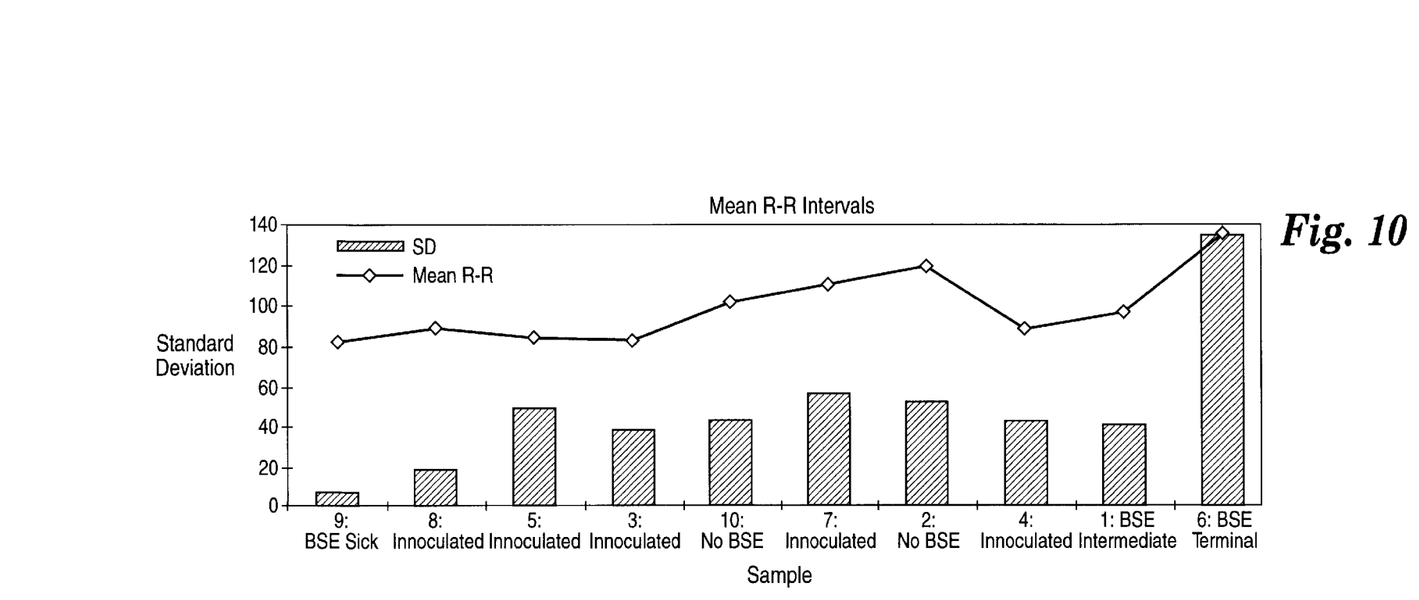
FIG. 10 represents the standard deviation and mean R-R intervals set out in the table of FIG. 9.
Figure 11:
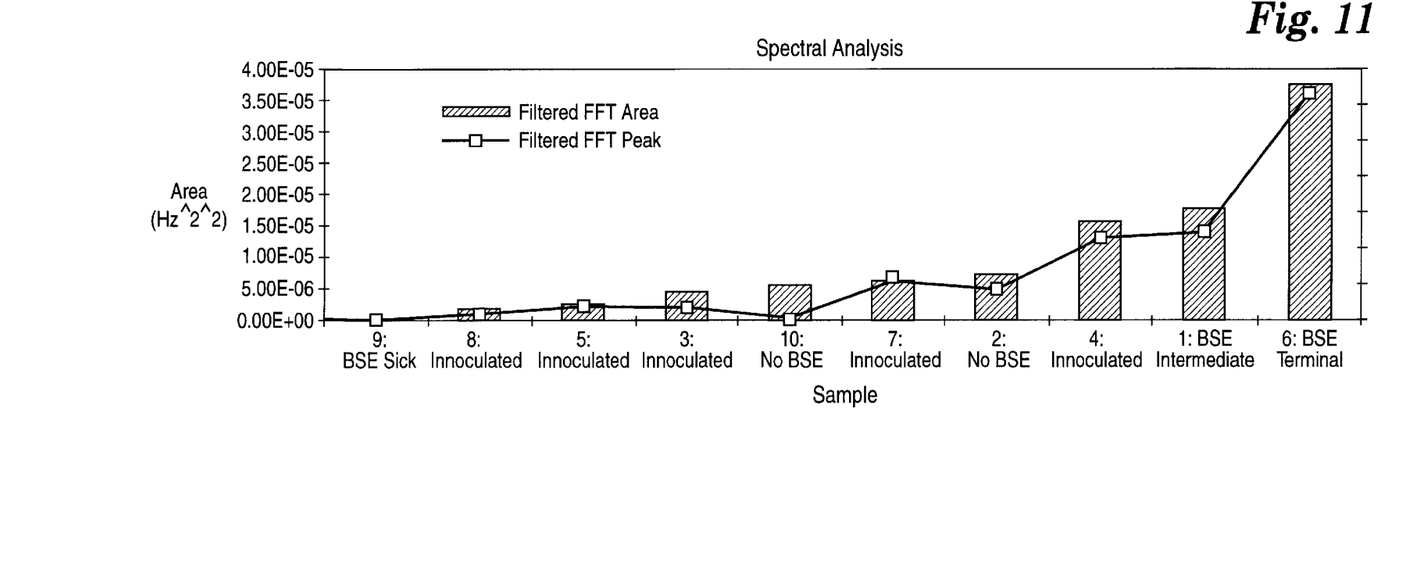
FIG. 11 represents the filtered FFT areas and peaks set out in the table of FIG. 9.

Data derived from each of the ten cows in the sample is presented in FIG. 9. It will be seen that animals 9 and 6 show extremely disrupted levels of HRV which correlates well with the fact that these two animals were exhibiting immediately apparent symptoms of BSE. No clear pattern was apparent in the case of the inoculated animal 5 and further analysis of results from those animals would be required to enable the development of the disease over time to be correlated with changes in the monitored HRV. The results do however provide strong support for the suggestion that HRV analysis may form the basis for a reliable non-invasive simple test for BSE in the field.

The text of this patent specification has focused on bovine spongiform encephalopathy but it will be appreciated that the invention is equally applicable to any degenerative brain disease in which lesions are formed progressively in the brain. Specifically the invention is applicable to the detection of any transmissible spongiform encephalopathy.

What is claimed is:

1. A method for selecting mammalian animal carcasses for introduction into the human food chain, comprising the steps of:

measuring the respiratory sinus arrhythmia of the animals to be slaughtered before slaughter; and, selecting only those carcasses from animals for which the associated RSA is normal.

2. A method according to claim 1, wherein the animal carcasses are selected if the RSA is within a predetermined range.

3. A method for selecting mammalian animals for slaughter, comprising the steps of:

assessing the respiratory sinus arrhythmia of the animals; and, slaughtering the animals which have an abnormal measured RSA.

4. A method according to claim 3, wherein animals are slaughtered if the measured RSA is outside a predetermined range.

5. An animal carcass selection apparatus, comprising means for monitoring the respiratory sinus arrhythmia of animals prior to slaughter, and means for generating an output representing whether or not individual animals have normal RSA, the output being used to enable the selection of carcasses of only those animals for which the output indicates normal RSA.

6. A selection apparatus for selecting animals for slaughter, comprising means for monitoring respiratory sinus arrhythmia of the animals, and means for producing an output indicating which animals have an abnormal measured RSA to enable the slaughter of such animals.

* * * * *